United States Patent [19]

Patel

[11] Patent Number: 5,476,650
[45] Date of Patent: Dec. 19, 1995

[54] CONDITIONING AND STRAIGHTENING HAIR RELAXER

[75] Inventor: Manilal M. Patel, DesPlaines, Ill.

[73] Assignee: Luster Products, Inc., Chicago, Ill.

[21] Appl. No.: 402,301

[22] Filed: Mar. 9, 1995

Related U.S. Application Data

[63] Continuation of Ser. No. 210,133, Mar. 17, 1994, abandoned.

[51] Int. Cl.$^6$ .................. A61K 7/09; A61K 7/07
[52] U.S. Cl. .................. 424/70.2; 424/70.4; 424/70.28; 424/70.16; 424/70.17; 132/204; 132/205
[58] Field of Search ................ 424/70.16, 70.2, 424/70.4, 70.17, 70.28; 132/204, 205

[56] References Cited

U.S. PATENT DOCUMENTS

| | | | |
|---|---|---|---|
| 3,738,913 | 6/1973 | Johnsen et al. | 195/29 |
| 3,904,748 | 9/1975 | Eckert et al. | 424/70 |
| 3,958,581 | 5/1976 | Abegg et al. | 132/7 |
| 3,959,463 | 5/1976 | Nersesian et al. | 424/70 |
| 4,148,329 | 4/1979 | Jaskowski | 152/7 |
| 4,175,572 | 11/1979 | Hsiung | 132/7 |
| 4,186,188 | 1/1980 | Gumprecht et al. | 424/70 |
| 4,237,910 | 12/1980 | Khahil et al. | 132/7 |
| 4,269,824 | 5/1981 | Villamarin et al. | 424/70 |
| 4,279,996 | 7/1981 | Yoshioka et al. | 424/70 |
| 4,304,244 | 12/1981 | de la Guardia | 132/7 |
| 4,324,263 | 4/1982 | de la Guardia | 132/7 |
| 4,369,037 | 1/1983 | Matsunaga et al. | 8/127.51 |
| 4,373,540 | 2/1983 | de la Guardia | 424/89 |
| 4,390,033 | 6/1983 | Khalil et al. | 132/7 |
| 4,416,297 | 11/1983 | Wolfram et al. | 132/7 |
| 4,454,060 | 6/1984 | Lai et al. | 252/547 |
| 4,494,557 | 1/1985 | Nagel | 132/7 |
| 4,507,280 | 3/1985 | Pohl et al. | 424/70 |
| 4,529,586 | 7/1985 | De Marco et al. | 424/70 |
| 4,540,507 | 9/1985 | Grollier | 252/174.23 |
| 4,602,648 | 7/1986 | Syed et al. | 132/7 |
| 4,612,188 | 9/1986 | Zorayan et al. | 424/47 |
| 4,663,158 | 5/1987 | Wolfram et al. | 424/70 |
| 4,710,374 | 12/1987 | Grollier | 424/70 |
| 4,867,966 | 9/1989 | Grollier et al. | 424/71 |
| 4,871,530 | 10/1989 | Grollier et al. | 424/47 |
| 4,883,657 | 11/1989 | Williams et al. | 424/72 |
| 4,996,997 | 3/1991 | Williams et al. | 132/204 |
| 5,171,565 | 12/1992 | Akhtar | 424/71 |
| 5,293,885 | 3/1994 | Darkawa | 132/209 |
| 5,304,370 | 4/1994 | Hankins | 424/71 |
| 5,338,540 | 8/1994 | Lee | 424/71 |

FOREIGN PATENT DOCUMENTS 0053448  11/1980  European Pat. Off. .

OTHER PUBLICATIONS

"Chemical Reformation Chemical Relaxing"; 1978; *Instructor Text* Redken Laboratories, Inc.; pp. 35–43.
Marvin K. Cook; "Modern Negro Cosmetics II"; May 1970; *Drug & Cosmetic Industry*; pp. 42–44.
"Protein Derivatives—Moisture and That Look of Youth"; Dec. 1969; *Aerosol Age*; pp. 30–36.

*Primary Examiner*—Thurman K. Page
*Assistant Examiner*—Sally Gardner
*Attorney, Agent, or Firm*—Brezina & Ehrlich

[57] ABSTRACT

A hair relaxing composition used in high alkaline conditions comprising at lease one active hair relaxer ingredient, moisturizers, emollients, and emulsifier, with polymethacrylamidopropyltrimonium chloride included in the formula.

8 Claims, No Drawings

CONDITIONING AND STRAIGHTENING HAIR RELAXER

This application is a continuation of Ser. No. 08/210,133 filed Mar. 17, 1994, now abandoned.

The present invention relates generally to a hair relaxing system, and more particularly to a hair relaxer system including a stable polyquaternium compound combined in the relaxer formula which provides conditioning factors such as wet combability and soft feel while working synergistically with the active ingredient to provide a highly efficient relaxer product.

BACKGROUND OF THE INVENTION

Calcium hydroxide based hair relaxer systems are commonly used for treatment of hair. However, it has been found that existing hair conditioning agents are often unstable and not substantive in the environment of the high pH levels (11.0 to 12.5, and sometimes higher) of the relaxer system required for relaxing the hair. The inclusion of conditioning ingredients in relaxer systems is preferred to provide detangling and enhanced wet combability by adding a substantive coating to the hair shaft.

Presently, many relaxer systems provide for the addition of a hair conditioning agent either pre or post application of the relaxer ingredient, which agent is added separately from the relaxer ingredient itself.

Therefore, present hair relaxer systems which include a separate pre or post conditioner require several steps to complete application of the system, with the conditioning agents added to the hair separately before or after the relaxing agents are applied. These multiple steps unnecessarily increase the time involved in applying the complete system.

Additionally, the use of a separate pre-conditioning step in relaxer systems allows for potential inconsistent results because the relaxer ingredients are applied directly over the preconditioner, diluting the relaxer and producing slowdown in the action of the relaxer. This dilution factor changes each time the process is applied to the hair and scalp.

Based upon known literature, the only agent that promotes conditioning while the relaxer is active is a cationic polymer, polyquaternium 6, available under the brand name Merquat 100. Such a system is disclosed in U.S. Pat. No. 4,175,572. However, the Merquat 100 polymer doesn't provide synergy with the active ingredients in the system to promote a more efficient relaxing process whereby the relaxer can have reduced active ingredient levels, yet provide faster processing time with less potential for hair damage.

Therefore, an object of the present invention is to provide a hair relaxer system that provides excellent wet combability and soft feel utilizing a stable polyquaternium compound that works synergistically with the active relaxer ingredients to provide a more efficient hair relaxer.

Another object of the present invention is to provide a hair relaxer system that leaves the relaxed hair soft and manageable, allowing for easy comb-out and less damage from tangling, knotting, and the like.

A further object of the present invention is to provide a hair relaxer system which effectively relaxes the hair with less active ingredients compared to products presently on the market, thereby reducing the possibility of irritation and overprocessing.

Another object of the present invention is to provide a hair relaxer system which includes a conditioning agent which conditions the hair prior to and during the relaxing process, and eliminates the need for the time-consuming application of a preconditioning agent.

In prior systems, there is no way to gage how much conditioner is on the hair, resulting in a change in the dilution factor each time the relaxing process is repeated. In the present invention, the conditioning system is built into the relaxer system, providing a constant level of active ingredients and consistent results.

SUMMARY OF THE INVENTION

The present invention is based on the discovery that a cationic polymer, namely polymethacrylamidopropyltrimonium chloride, when added to a high pH hair relaxer system, provides a conditioning ingredient which remains stable throughout the relaxing process, and works synergistically before, during and after the relaxing process with active ingredients in the relaxer system to increase the efficiency of the relaxing process, and to provide less potential for irritation and over processing. The hair relaxer of the present invention, in one preferred embodiment, comprises an aqueous dispersion containing from about 35–55 percent by weight of deionized water, from about 10–30 percent by weight of mineral oil, from about 5–12 percent by weight of cetearyl alcohol, from about 5–30 percent by weight of petrolatum, from about 3–7 percent by weight of an active hair relaxer composition such as calcium hydroxide for example, from about 2–6 percent by weight of propylene glycol, from about 0.1–2 percent by weight of DEA oleth-10 phosphate, from about 0.5–3 percent by weight of cetyl alcohol, from about 0.1–2 percent by weight of PEG-75 lanolin, from about 0.1–5 percent by weight of ceteareth –20, and from about 0.1–15 percent by weight of polymethacrylamidopropyltrimonium chloride, alone or in combination with calcium hydroxide.

In an alternate embodiment of the invention, sodium hydroxide is used in place of calcium hydroxide in the above formula, ceteareth –20 is removed, and small changes in the ingredient percentages are made. In another alternate embodiment, lithium hydroxide monohydrate is included as an active relaxer ingredient, alone or in combination with calcium hydroxide.

The above relaxer composition is a relatively high alkaline hair relaxing process.

The cationic polymer used in the percentages set forth hereinbelow has been found to be unexpectedly stable at pH values between 11.5 and 12.5 before the activator is added. Upon addition of the activator, the pH of the system increases, and the cationic polymer remains stable. Also, the cationic polymer has been observed to aid in the speed and the results of the hair relaxing process.

DETAILED DESCRIPTION OF THE PREFERRED EMBODIMENT

The hair relaxer composition of this invention, in a preferred embodiment, comprises an aqueous dispersion containing from about 35–55 percent by weight of deionized water, from about 10 10–30 percent by weight of mineral oil, from about 5–12 percent by weight of cetearyl alcohol, from about 5–30 percent by weight of petrolatum, from about 3–7 percent by weight of calcium hydroxide, from about 2–6 percent by weight of propylene glycol, from about 0.1–2 percent by weight of DEA oleth-10 phosphate, from about 0.5–3 percent by weight of cetyl alcohol, from about 0.1–2 percent by weight of PEG-75 lanolin, from about 0.1–5 percent by weight of ceteareth –20, and from about 0.1–15 percent by weight of polymethacrylamidopropyltrimonium chloride.

The above composition is used in conjunction with a mix activator which comprises an aqueous dispersion consisting of from about 60–85 percent by weight deionized water, from about 15–35 percent by weight guanidine carbonate, from about 0.0001–2 percent by weight of xanthan gum, and from about 0.00001–1 percent by weight of D&C Red #40. Guanidine carbonate is mixed with calcium hydroxide to form the guanidine hydroxide in the above composition.

In the above relaxer formula, the mineral oil acts as an emollient, the cetearyl alcohol is an emulsifier, petrolatum is a moisturizer, the calcium hydroxide is the active relaxer ingredient, DEA Oleath –10 phosphate is an active emulsifier/emollient, the cetyl alcohol is a secondary emulsifier, the PEG-75 lanolin is an emollient, the cetearth-20 is an emulsifier, and the polymethacrylamidopropyltrimonium chloride is a conditioning agent which mitigates hair damage by helping to facilitate the penetration of conditioner agents into the hair shaft during the relaxing process. The conditioner ingredient, which is a cationic polymer, provides further protection due to its substantivity to keratin protein. The conditioner also works synergistically with the guanidine hydroxide relaxer to provide faster and more thorough relaxing.

In the use of this first embodiment of the invention, the relaxer formula is mixed with the activator composition, resulting in a mixture having a pH in the range of 12.50 to 12.95. After mixing, the combined ingredients are applied to the hair and left on the hair for approximately 12 to 20 minutes. After completion of the relaxing process, an acidic shampoo is applied to the hair to remove excess alkaline solution from the hair.

A second embodiment of the present invention comprises a relaxer in an aqueous dispersion containing from about 35–55 percent by weight of deionized water, from about 20–30 percent by weight of petrolatum, from about 10–30 percent by weight of mineral oil, from about 5–12 percent by weight of cetearyl alcohol, from about 1–3 percent by weight of sodium hydroxide, from about 2–6 percent by weight of propylene glycol, from about 0.1–2 percent by weight of DEA oleth-10 phosphate, from about 0.5–3 percent by weight of cetyl alcohol, from about 0.1–2 percent by weight of PEG-75 lanolin, and from about 0.1–15 percent by weight of polymethacrylamidopropyltrimonium chloride.

In the formulation of the relaxer of the second embodiment, the active ingredient sodium hydroxide replaces calcium hydroxide in the formulation of the first embodiment, and the emulsifier cetearth –20 is absent from the second relaxer formulation. Each of the remaining ingredients in the second formulation performs the same function as in the first formulation. Also, in the second formulation, there is a slight variance in the percentage range by weight of the ingredients compared to the first embodiment.

The relaxer of the second embodiment is a no-mix conditioning relaxer which is not used in combination with the activator mixture described above.

A third embodiment of the present invention comprises a further no-mix conditioning relaxer in an aqueous dispersion containing from about 35–55 percent by weight of deionized water, from about 5–30 percent by weight of petrolatum, from about 5–15 percent by weight of a mixture of cetearyl alcohol and ceteareth-20, from about 1–4 percent by weight of lithium hydroxide monohydrate, from about 1–5 percent by weight of calcium hydroxide, from about 1–6 percent by weight of propylene glycol, from about 0.1–2 percent by weight of DEA-oleth-10 phosphate, from about 0.5–3 percent by weight of cetyl alcohol, from about 0.2–2 percent by weight of PEG-75 lanolin and from 0.1–15 percent by weight of polymethacrylamidopropyltrimonium chloride.

In the formulation of the relaxer of the third embodiment, the active ingredient lithium hydroxide monohydrate is added to the ingredients comprising the formula of the first embodiment. The lithium hydroxide monohydrate is an active relaxer ingredient along with the calcium hydroxide in the formula. The remaining ingredients in the formula perform the same function as described above relating to the first embodiment of the invention. The formulation of the third embodiment is not mixed with an activator prior to use.

The presently disclosed cationic polymer, polymethacrylamidopropyltrimonium chloride, can be used in additional relaxer formulas where lithium hydroxide alone or potassium hydroxide forms the active relaxer ingredient.

The following examples further illustrate the present invention.

EXAMPLE I

A hair relaxing composition was prepared having the following composition:

|  | Weight Percent |
|---|---|
| Cetearyl Alcohol and Ceteareth-20 | 11.00% |
| Cetyl Alcohol | 1.00% |
| PEG-75 Lanolin | 0.50% |
| Mineral Oil | 24.00% |
| Petrolatum | 5.00% |
| DEA-Oleth-10 Phosphate | 0.50% |
| Deionized Water | 48.30% |
| Propylene Glycol | 3.00% |
| Calcium Hydroxide | 5.70% |
| Polymethacylamidopropyl-trimonium Chloride | 1.00% |

A color mix activator composition was prepared having the following composition:

|  |  |
|---|---|
| Deionized Water | 75.90% |
| Guanidine Carbonate | 24.00% |
| Xanthan Gum | 0.10% |
| D&C Red #40 | 0.0018% |

EXAMPLE II

A hair relaxing composition was prepared having the following composition:

|  | Weight Percent |
|---|---|
| Cetearyl Alcohol | 10.00 |
| Cetyl Alcohol | 1.00 |
| PEG-75 Lanolin | 1.00 |
| Mineral Oil | 14.00 |
| Petrolatum | 22.00 |
| DEA-Oleth-10 Phosphate | 0.50 |
| Deionized Water | 44.40 |
| Propylene Glycol | 3.00 |

-continued

|  | Weight Percent |
|---|---|
| Sodium Hydroxide | 2.10 |
| Polymethacrylamidopropyl-trimonium Chloride | 2.00 |

No color mix activator is required when using the formulation of Example II.

EXAMPLE III

A hair relaxing system was prepared having the following composition:

|  | Weight Percent |
|---|---|
| Cetearyl Alcohol and Ceteareth-20 | 10.00% |
| Cetyl Alcohol | 1.00% |
| PEG-75 Lanolin | 0.50% |
| Mineral Oil | 24.00% |
| Petrolatum | 10.00% |
| DEA-Oleth-10 Phosphate | 0.50% |
| Deionized Water | 44.45% |
| Propylene Glycol | 3.00% |
| Lithium Hydroxide Monohydrate | 2.75% |
| Calcium Hydroxide | 1.80% |
| Polymethacylamidopropyl-trimonium Chloride | 2.00% |

No color mix activator is required when using the formulation of Example III.

The procedure for use of the hair relaxer system of Example I is as follows: First, mix the relaxer and color mix activator compositions thoroughly until the mixture is totally smooth and free of lumps. Next, part the hair in four equal sections. Start in the back section and separate the hair into approximately ¼ inch partings. Apply a generous amount of relaxer mixture from the root to the end of the hair starting with the first parting, with the back of a wide toothed comb. The relaxer mixture is applied over the entire hair shaft, section by section.

Smooth all hair using short, firm strokes, from the scalp to the end of the hair shaft. Leave the mixture on the hair from between 10 to 28 minutes, depending upon hair texture, timing from the start of application.
Fine hair: 10 to 15 minutes
Medium hair: 15 to 20 minutes
Course hair: 20 to 28 minutes
Then, rinse hair thoroughly with warm water to remove all of the mixture. To ensure that all of the mixture is removed, preferably rinse the hair two or three times. Next, apply shampoo to the hair and rinse completely to remove any residue of relaxer remaining on the hair.

The above steps are used to apply the relaxer system to virgin, or non-previously relaxed hair. If the system is to be used for new growth hair, or retouched hair, half as much relaxer and activator is used, and the remaining steps remain the same.

The procedure for application of the hair relaxer systems of Examples II and III above is the same as described for Example I, except that Examples II and III are no-mix systems, and the step of mixing the relaxer with the color mix activator composition is eliminated.

We claim:

1. A hair relaxing composition for use in alkaline conditions comprising an aqueous dispersion containing from about 35–55 percent by weight of deionized water, from about 10–30 percent by weight of mineral oil, from about 5–12 percent by weight of cetearyl alcohol, from about 5–30 percent by weight of petrolatum, from about 3–7 percent by weight of calcium hydroxide, from about 2–6 percent weight of propylene glycol, from about 0.1–2 percent by weight of DEA oleth-10 phosphate, from about 0.5–3 percent by weight of cetyl alcohol, from about 0.1–2 percent by weight of PEG-75 lanolin, from about 0.1–5 percent by weight of ceteareth –20, and from about 0.1–15 percent by weight of polymethacrylamidopropyltrimonium chloride.

2. The hair relaxing composition of claim 1 wherein said cetearyl alcohol and ceteareth-20 is present in the amount of 11 weight percent, said cetyl alcohol is present in the amount of 1 weight percent, said PEG-75 lanolin is present in the amount of 0.5 weight percent, said mineral oil is present in the amount of 24 weight percent, said petrolatum is present in the amount of 5 weight percent, said DEA oleth-10 phosphate is present in the amount of 0.5 weight percent, deionized water is present in the amount of 48.3 weight percent, said propylene glycol is present in the amount of 3 weight percent, said calcium hydroxide is present in the amount of 5.7 weight percent, and said polymethacrylamidopropyltrimonium chloride is present in the amount of 1 weight percent.

3. A hair relaxing composition used in alkaline conditions comprising an aqueous dispersion containing from about 35–55 percent by weight of deionized water, from about 10–30 percent by weight of mineral oil, from about 5–12 percent by weight of cetearyl alcohol, from about 20–30 percent by weight of petrolatum, from about 1–3 percent by weight of sodium hydroxide, from about 2–6 percent by weight of propylene glycol, from about 0.1–2 percent by weight of DEA oleth-10 phosphate, from about 0.5–3 percent by weight of cetyl alcohol, from about 0.1–2 percent by weight of PEG-75 lanolin, and from about 0.1–15 percent by weight of polymethacrylamidopropyltrimonium chloride.

4. The hair relaxing composition of claim 3 wherein deionized water is present in the amount of 44.4 weight percent, mineral oil is present in the amount of 14 weight percent, cetearyl alcohol is present in the amount of 10 weight percent, petrolatum is present in the amount of 22 weight percent, sodium hydroxide is present in the amount of 2.1 weight percent, propylene glycol is present in the amount of 3.0 weight percent, DEA oleth-10 phosphate is present in the amount of 0.5 weight percent, cetyl alcohol is present in the amount of 1.0 weight percent, PEG-75 lanolin is present in the amount of 1.0 weight percent, and polymethacrylamidopropyltrimonium chloride is present in the amount of 2.0 weight percent.

5. A hair relaxing composition used in alkaline conditions comprising an aqueous dispersion containing from about 35–55 percent by weight of deionized water, from about 10–30 percent by weight of mineral oil, from about 5–15 percent by weight of a combination of cetearyl alcohol and ceteareth-20, from about 5–30 percent by weight of petrolatum, from about 1–4 percent by weight of lithium hydroxide monohydrate, from about 1–5 percent by weight of calcium hydroxide, from about 1–6 percent by weight of propylene glycol, from about 0.1–2 percent by weight of DEA oleth-10 phosphate, from about 0.5–3 percent by weight of cetyl alcohol, from about 0.2–2 percent by weight of PEG,75 lanolin, and from about 0.1–15 percent by weight of polymethacrylamidopropyltrimonium chloride.

6. The hair relaxing composition of claim 5 wherein the combination of cetearyl alcohol and ceteareth-20 is present in the amount of 10 weight percent, said cetyl alcohol is present in the amount of 1 weight percent, said PEG-75 lanolin is present in the amount of 1.0 weight percent, said mineral oil is present in the amount of 24 weight percent, said petrolatum is present in the amount of 10 weight percent, said DEA oleth-10 phosphate is present in the amount of 0.5 weight percent deionized water is present in the amount of 44.45 weight percent, said propylene glycol is present in the amount of 3 weight percent, said lithium hydroxide monohydrate is present in the amount of 2.75 weight percent, said calcium hydroxide is present in the amount of 1.8 weight percent, and said polymethacrylamidopropyltrimonium chloride is present in the amount of 2 weight percent.

7. A method of relaxing hair comprising the steps of:

(a) mixing the composition of claim 1 with an aqueous dispersion of about 60–85 percent by weight water, about 15 to 35 percent by weight guanidine carbonate, about 0.0001–2 percent by weight xanthan gum and from about 0.00001–1 percent by weight of D&C Red #40 to provide an aqueous dispersion having a pH of 12.50 to 12.95;

(b) applying the aqueous dispersion to the hair for about 10 to about 28 minutes, and (c) shampooing the hair with an acidic shampoo to neutralize and remove the aqueous dispersion from the hair.

8. A method of relaxing hair comprising the steps of:

(a) mixing the composition of claim 6 with an aqueous dispersion of about 60–85 percent by weight water, about 15 to 35 percent by weight guanidine carbonate, about 0.0001–2 percent by weight xanthan gum and from about 0.00001–1 percent by weight of D&C Red #40, to provide an aqueous dispersion having a pH of 12.50 to 12.95;

(b) applying the aqueous dispersion to the hair for about 10 to about 28 minutes, and (c) shampooing the hair with an acidic shampoo to neutralize and remove the aqueous dispersion from the hair.

* * * * *